Figure 1:
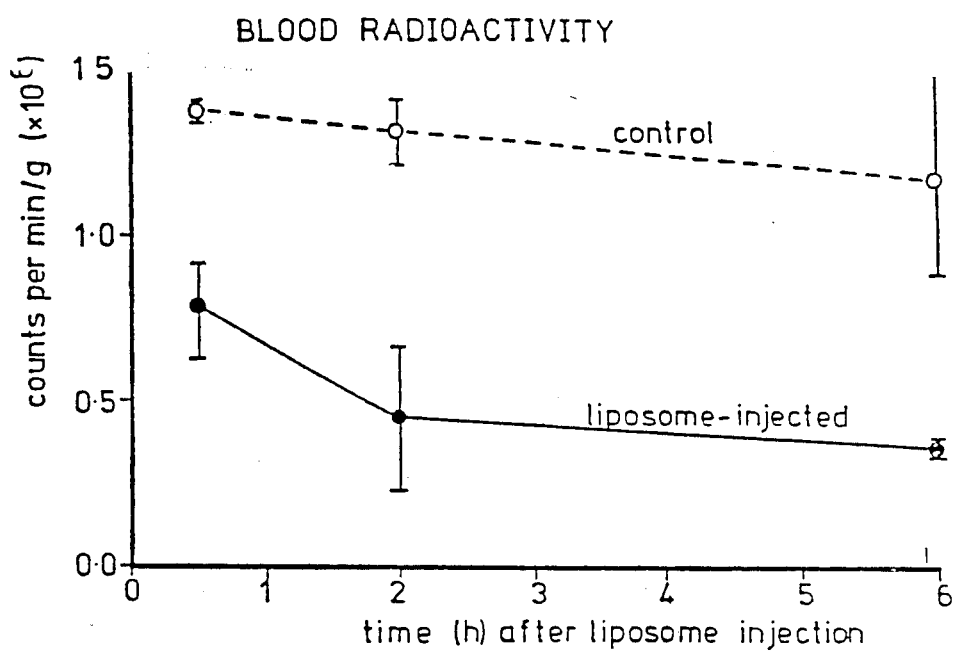

United States Patent [19]

Begent

[11] Patent Number: 4,865,835
[45] Date of Patent: Sep. 12, 1989

[54] DIAGNOSIS AND TREATMENT OF TUMORS

[76] Inventor: Richard H. J. Begent, 14 Southdean Gardens, London S.W.19, England

[21] Appl. No.: 866,955

[22] Filed: May 27, 1986

Related U.S. Application Data

[63] Continuation of Ser. No. 384,372, Jun. 2, 1982, abandoned.

[51] Int. Cl.$^4$ .................... A61K 49/00; A61K 49/02; A61K 9/50; A61K 39/44
[52] U.S. Cl. ......................................... 424/1.1; 424/9; 424/450
[58] Field of Search ................... 424/1.1, 9, 85, 450; 128/1.1; 436/829

[56] References Cited

U.S. PATENT DOCUMENTS

| | | | |
|---|---|---|---|
| 3,993,754 | 11/1976 | Rahman et al. | 424/177 |
| 4,291,024 | 9/1981 | Turcotte | 424/180 |
| 4,310,505 | 1/1982 | Baldeschwieler et al. | 424/1.1 |
| 4,310,506 | 1/1982 | Baldeschwieler et al. | 424/1.1 |
| 4,343,895 | 8/1982 | Sugaar | 435/6 |
| 4,377,567 | 3/1983 | Gelo | 424/1.1 |
| 4,472,371 | 9/1984 | Bwchiel et al. | 424/1.1 |
| 4,624,846 | 11/1986 | Goldenberg | 424/1.1 |

OTHER PUBLICATIONS

Ku et al., CA 93:110153e, 1980.
Papahajopoulos et al., CA 85:137237g, 1976.
Leserman et al., Proc. Natl. Acad. Sci. USA, 77(7), pp. 4089–4093, 1980.
Poste et al., Nature, 261 (5562), pp. 699–706, 1976.
Torchilin et al., Biochemical & Biophysical Research Comm., vol. 89 (4), pp. 1114–1119 (1979).
Gregoriadis et al., Biochemical & Biophysical Research Comm., vol. 65 (2), pp. 537–544 (1975).
Gregoriadis et al., Biochemical Society Transactions, vol. 3, pp. 613–618 (1975).
Begent et al.; Thelancet, Oct. 2, 1982, pp. 2–5.
Barratt et al.; Biochimica et Biophysica Acta 762 (1983) 154–164.

Primary Examiner—John F. Terapane
Assistant Examiner—J. E. Thomas
Attorney, Agent, or Firm—Cushman, Darby & Cushman

[57] ABSTRACT

There are disclosed liposomes to which are linked agents which are capable of binding an anti-tumor antibody. The liposomes are useful in the detection and treatment of tumors by reason of their ability to remove non-specifically distributed anti-tumor antibodies from vascular and other extra-cellular spaces.

14 Claims, 4 Drawing Sheets

DIAGNOSIS AND TREATMENT OF TUMORS

This is a continuation of application Ser. No. 384,372, filed June 2, 1982, now abandoned.

This invention relates to the diagnosis and treatment of tumours in human and non-human animals.

Antibodies directed against tumour products such as carcinoembryonic antigen (CEA) and human chorionic gonadotrophin (HCG) have been shown to bind to xenografts of human tumours in animals, and to tumours in human patients suffering from cancer. It has emerged from these studies that a very small proportion of the administered antibody is localised in the tumour, the remainder of the antibody being non-specifically distributed in vascular and other extra-cellular spaces. For example, Mach J-P et al found on one study in man that only 0.1% of administered antibody is localised in the tumour (New Eng. J. Med. 303, 5–10, 1238–9, 1980).

The non-specific distribution of anti-tumour antibodies represents a serious problem if it is desired to use anti-tumour antibodies for the detection of tumours.

One such method of detection, for example, involves the administration of radio-labelled anti-tumour antibodies which are then visualised by external scintigraphy. During this procedure, non-specifically distributed anti-tumour antibodies tend to mask the tumour-bound antibodies. In an attempt to minimise this problem, it is usual to administer a second radionuclide, usually $^{99m}$Tc in the form of $^{99m}$Tc-labelled albumin or free pertechnetate. The image given by the $^{99m}$Tc is then subtracted from that of the other radionuclide, usually $^{131}$I, with which the anti-tumour antibody is labelled. This method produces artifacts related to the different energies of the two radionuclides and to the different distribution of the two radionuclides in normal tissues.

The non-specific accumulation of anti-tumour antibody in vascular and other extra-cellular spaces also represents a major difficulty in certain areas of anti-tumour therapy. For example, therapy using $^{131}$I-labelled antibody to CEA in treatment of xenografts of the human colon carcinoma in experimental animals has been limited by a poor therapeutic ratio such that the antibody to CEA gave only marginally superior results to those obtained with non-specific immunoglobulin (Goldenberg et al, Cancer Res., 41, 4354–60, 1981).

It has now been found that the problem of non-specifically distributed anti-tumour antibodies can be very largely met by the use of liposomes to clear such non-specifically distributed antibodies from the system.

Liposomally-entrapped antibody to digoxin has been shown to be effective in removing digoxin from the circulation of experimental animals through clearance of liposomes by the reticuloendothelial system (Campbell et al., Eur. J. Biochem. 105, 87–92, 1980). The present invention is based on the discovery that liposomally-entrapped second antibody directed against the anti-tumour antibody is able to clear the latter rapidly from vascular and other extracellular spaces, but, most significantly, not from tumours to which the anti-tumour antibody is specifically bound.

According to the present invention, therefore, there is provided a liposome to which is linked an agent capable of binding an anti-tumour antibody.

The agent which is capable of binding the anti-tumour antibody is preferably itself an antibody, but it may, for example, be a cell-surface receptor for the anti-tumour antibody.

The anti-tumour antibody may, for example, be anti-carcinoembryonic antigen. A variety of other anti-tumour antibodies may be used, however, including monoclonal antibodies raised against tumour cells or extracts thereof.

The present invention also provides a method of treatment of tumours comprising administering to a patient an anti-tumour antibody, and subsequently administering to said patient a second agent, preferably an antibody, capable of binding said anti-tumour antibody, said second agent being linked to a liposome.

A further aspect of the present invention provides a method of locating tumours comprising administering to a patient a labelled anti-tumour antibody, and subsequently administering to said patient a second agent, preferably an antibody, capable of binding said anti-tumour antibody, said second agent being linked to a liposome.

The second agent may be linked to the liposomal surface by chemical means such as covalent linking. Preferably, however, the second agent is an antibody which is entrapped in the liposome.

For the treatment of tumours, the anti-tumour antibody may, if desired, be coupled to an anti-tumour agent such as cytostatic or cytotoxic drug or a radionuclide.

For the detection of tumours, the labelled anti-tumour antibody is preferably radio-labelled, for example, by means of $^{131}$I or $^{125}$I.

It has been found from studies on mice and rabbits that the rate of clearance of blood anti-tumour antibody was greatest (up to 50% clearance of pre-liposome levels) over the first two hours after injection of liposome-entrapped second antibody. The difference between the rate of clearance of anti-tumour antibody from blood of liposome-treated animals compared with untreated animals was also greatest over this period. For external scintigraphy of tumours, it is therefore preferred that scanning take place at least 2 hours after administration of the liposome-linked antibody. It is particularly preferred that scanning take place less than 48 hours, for example 24 hours, after administration of liposome-linked antibody.

Figure 2:
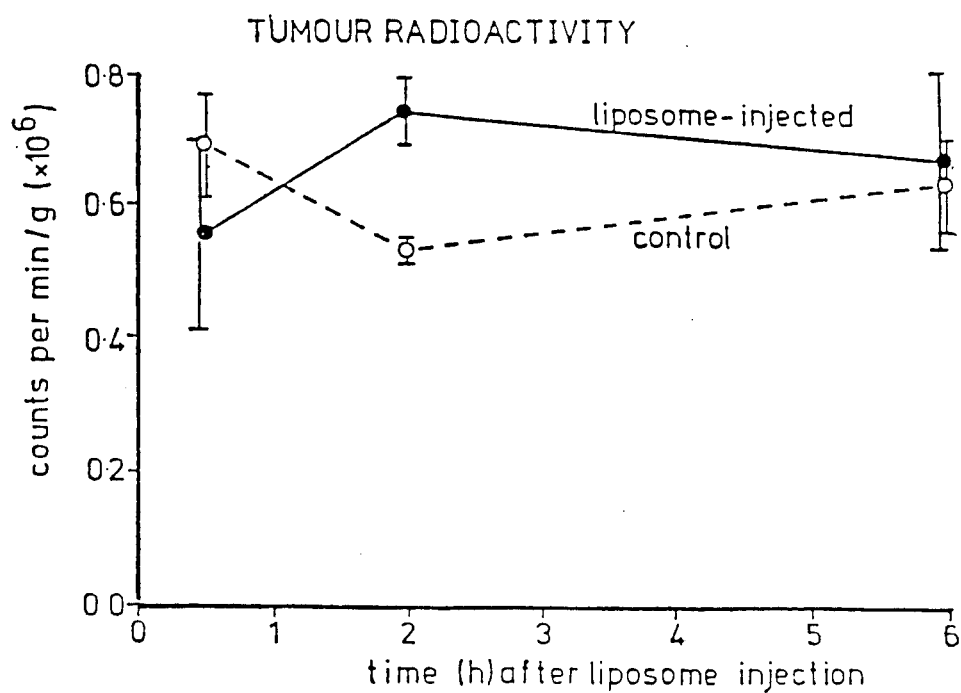
Figure 3:
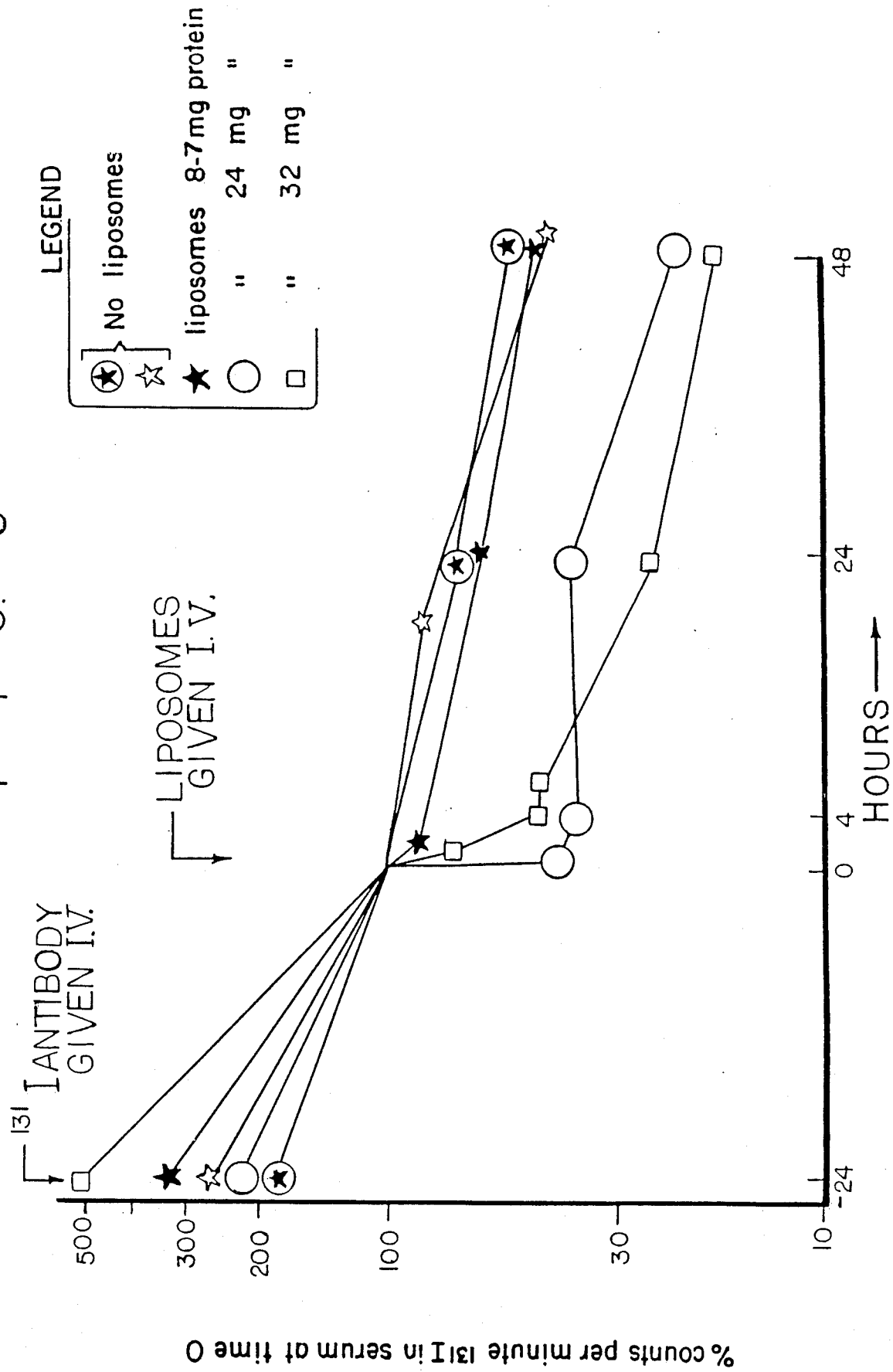

A method of preparation of the liposome-linked agent of the present invention, and the use of such a liposome-linked agent in the detection of tumours is now described, by way of example, with reference to the drawings, in which FIG. 1 is a graph illustrating liposomal clearance of $^{125}$I-labelled anti-CEA from blood of nude mice bearing human tumour TAF, FIG. 2 is a graph illustrating liposomal clearance of $^{125}$I-labelled anti-CEA from tumours of nude mice bearing human tumour TAF, FIG. 3 is a graph showing the relationship between the amount of liposome-linked antibody administered, and the rate of clearance of $^{131}$I-labelled anti-CEA from blood of humans with gastrointestinal cancer.

Figure 4:
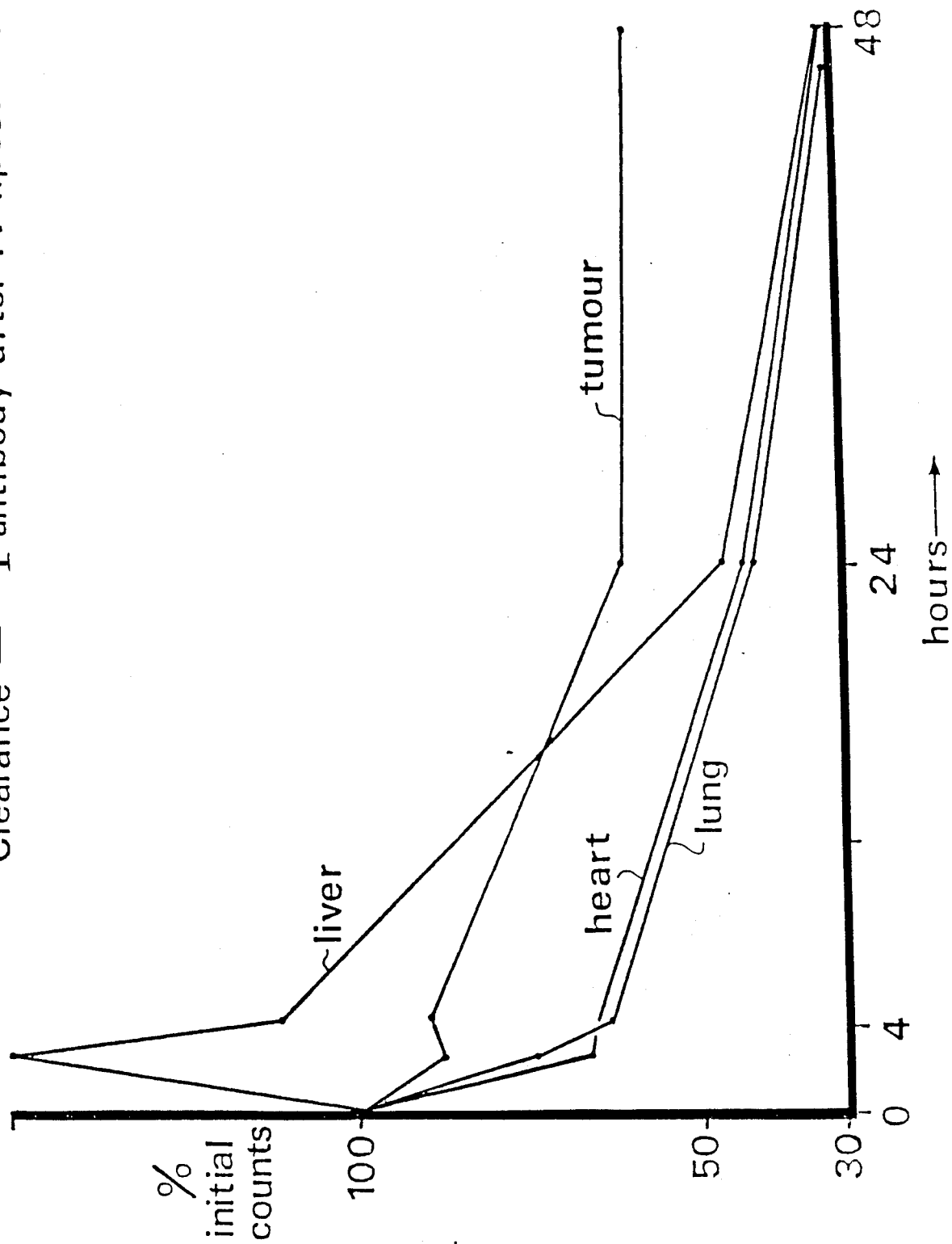
Figure 5:
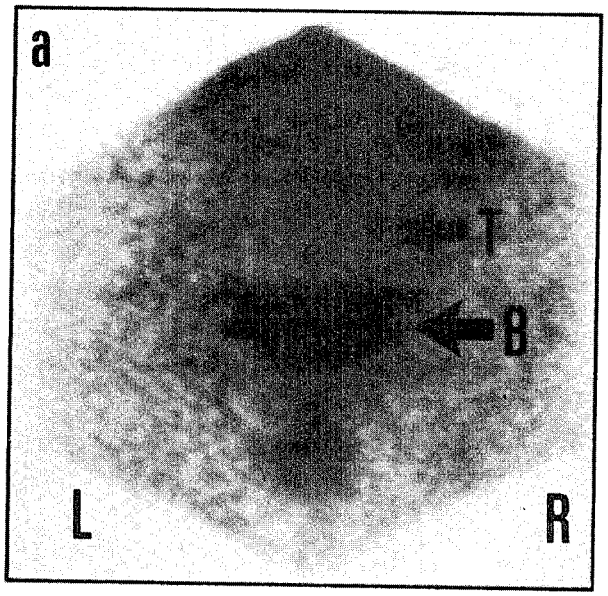
Figure 6:
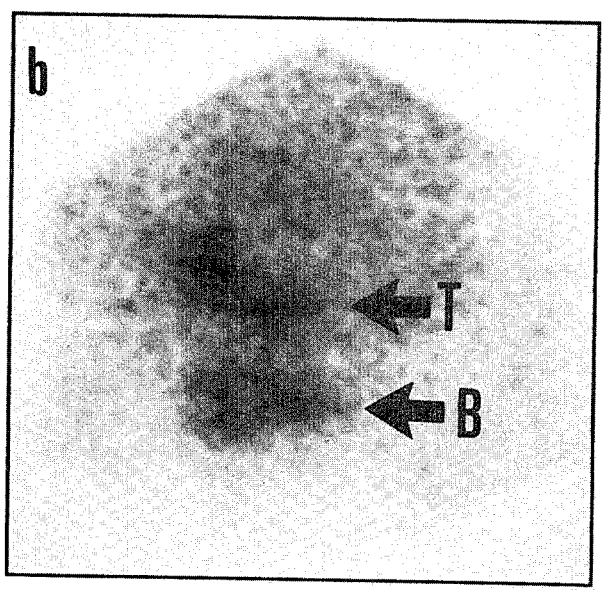

FIG. 4 shows clearance of $^{131}$I-labelled anti-CEA (as measured with a gamma camera) from different human organs before and at intervals after injection of liposome-linked antibody, FIG. 5 is a gamma camera image of a patient with a recurrence of rectal carcinoma, obtained with the patient sitting above the camera, and FIG. 6 is an image of the same region as is shown in FIG. 5, but 24 hours after intravenous administration of liposome-linked antibody.

EXAMPLE 1

Preparation of primary antibody.

Perchloric acid-extracted CEA, purified by gel filtration on Sephadex G-200 and by affinity chromatography on Con A-Sepharose (Keep et al., Br. J. Cancer 37, 171–182, 1978) was used for immunisation of a goat. The resulting antiserum (PK1G (D2)) was immunopurified on a CEA/Sepharose immunoadsorbent and absorbed with normal human spleen, liver, colon and plasma (Searle et al., Nuc. Med. Commun. 2, 131–139, 1980). The anti-CEA immunoglobulin was labelled with $^{125}$I in ice by the Chloramine-T technique (after Hunter and Greenwood, Nature 194, 495–496, 1962) to give a specific activity of 12 $\mu$Ci/$\mu$g antibody.

Preparation of Second antibody.

The $\gamma$-globulin fraction of horse anti-goat second antibody (BW402, gift of antiserum from Burroughs Wellcome Ltd.) was obtained by precipitation with ammonium sulphate and purified by DEAE-Sephadex gel chromatography.

Preparation of Liposomes.

Negatively charged liposomes were prepared by the method of Gregoriadis and Ryman (Biochem. J. 129, 123–133, 1972) using egg phosphatidylcholine, chlolesterol and phosphatidic acid in the molar ratio 9:9:2 and 5 mM phosphate buffer, pH 7.4 containing sodium chloride (9 g/l) and second antibody $\gamma$-globulin (10 g/l). In some experiments (table IV) $^{14}$C-chlolesterol was added as a marker of liposome lipid. The liposomes were sonicated for 10 min with cooling (MBE "Soniprep" probe 7$\mu$ peak to peak amplitude for 20 bursts of 30 seconds interspersed with 30 seconds cooling and free second antibody was separated from liposome-entrapped protein by gel filtration on Sepharose CL-6B. In preliminary experiments a trace of $^{125}$I-second antibody labelled by the Chloramine-T technique after Hunter and Greenwood, 1968, was added to the aqueous medium. In one experiment (table III) the liposome bilayer was labelled with $^{99m}$Tc by the method of Richardson et al, (J. Nuc. Med. 19, 1049–1054, 1978). Liposomes prepared in this way contained 126 $\mu$g of second antibody per $\mu$mole of liposomal lipid. The ability of the liposomes to bind primary antibody was determined by titration curves of liposome-entrapped second antibody, free second antibody and liposomes containing no second antibody (controls) with $^{125}$I-labelled goat anti-CEA immunoglobulin. Filtration of the immune complexes, counting and analysis were performed on the Kemtek automated radioimmunoassay system (Bagshawe, Laboratory Practice 23, 573–575, 1974). Liposomes containing no anti-goat second antibody did not bind primary antibody. The amount of $^{125}$I-primary antibody bound by liposome-entrapped second antibody was only 4% of that bound by an equal concentration of second antibody free in solution.

Lipsomal clearance of labelled primary antibody

Mice: Groups of normal AKR mice, or nude mice bearing xenografts of a poorly-differentiated human colonic adenocarcinoma (TAF, a Charing Cross line) or xenografts of a moderately well-differentiated human colonic adenocarcinoma (P116, Cobb, Br. J. Cancer 28, 400, 1973; Lewis and Keep, Br. J. Cancer (in press) 1981) were given intravenous injections of $^{125}$I-labelled primary goat anti-CEA antibody (10–20 $\mu$Ci; 0.9–1.7 $\mu$g). Twenty four hours later, half the animals received liposomes containing second antibody intravenously (3–27 $\mu$mole lipid as liposomes in 0.1–0.2 ml; 378–3402 g second antibody $\gamma$-globulin), the rest remained as controls. Mice were killed at intervals up to 24 h after injection of liposomes, tissues were removed and the distribution of $^{125}$I, and in some cases $^{14}$C and $^{99m}$Tc determined. The results are expressed in FIGS. 1 and 2, and tables I–IV (3 animals per point unless stated).

Rabbits: Seven rabbits each received $^{125}$I-labelled normal goat immunoglobulin (labelled as described for anti-CEA; 16–18 $\mu$Ci, 4 $\mu$g, 0.2 ml). After 24 h, (a) three rabbits (nos. 1–3) were injected intravenously with liposomes containing second antibody (22.5 mg liposomes containing 30 $\mu$mole lipid; 4.7 mg immunoglobulin), (b) two rabbits (nos. 4 and 5) received liposomes containing no second antibody (30 $\mu$mole lipid) and (c) two rabbits (nos 6 and 7) received no liposomes. Blood (2 ml) was taken from each rabbit at intervals before and after liposome administration and the $^{125}$I activity determined. The results are expressed in table V. The rabbits were observed daily and their temperature monitored.

RESULTS

For xenograft-bearing mice, less $^{125}$I activity was present in the blood of liposome-treated mice than in the blood of controls at 30 min and at all subsequent times after liposome injection (FIG. 1, table I). This was also true for normal mice where the tissues were excised 4 h after administration of liposomes (table II). In tumour-bearing animals clearance of labelled primary antibody was related to liposome dose FIG. 2 (table I). In mice given 10 $\mu$mole lipid (1260 $\mu$g $\gamma$-globulin) the blood radioactivity was 25–30% of that in controls, and in animals given 27 $\mu$mole lipid (3402 $\mu$g $\gamma$-globulin) the blood $^{125}$I activity was only 5% of the control 24 h after treatment.

In tumour-bearing mice there was no difference between the $^{125}$I counts in the tumours of the control group and the counts in the tumours of mice treated with liposome-entrapped second antibody, up to 6 h after treatment (table I). Twenty four hours after liposome injection the tumour radioactivity in animals given entrapped second antibody was less than that in the control animals. However, the tumour to blood ratio of primary antibody was still increased relative to the controls (table I).

Markers of the liposome bilayer, $^{14}$C-cholesterol and $^{99m}$Tc, were removed rapidly from the blood of mice after injection and accumulated in the liver and spleen. (tables III and IV). From the distribution of $^{14}$C-cholesterol, it appeared that liposomes were not accumulated within the tumours (table IV).

In rabbits, 2 h after liposome-entrapped second antibody was injected, the blood $^{125}$I activity dropped by 28–42% (table V). In the controls (empty liposomes or no liposomes), the blood $^{125}$I activity dropped by 5–20% over the same period. Overall the blood radioactivity was cleared fastest when liposomes containing entrapped second antibody were administered. In rabbits given liposome-entrapped second antibody, the blood $^{125}$I levels were down to 10% of pre-liposome levels approximately 140 h after liposome administration. No adverse effects of liposome treatment were observed, and the rabbits' temperatures remained normal.

TABLE 1

$^{125}I$ distribution in nude mide bearing human colonic tumour xenografts, after treatment with liposome-entrapped second antibody

| Tumour line | Liposome dose (μmole lipid) | Time after liposome injection (h) | Tissue radioactivity (cpm/g) % (liposome-treated controls) Blood | Tissue radioactivity (cpm/g) % (liposome-treated controls) Tumour | Ratio of tumour radioactivity to blood radioactivity Control | Ratio of tumour radioactivity to blood radioactivity Liposome-treated |
|---|---|---|---|---|---|---|
| P116 | 3 | 6 | 30 | 122 | 0.30 | 1.22 |
|  |  | 24 | 39 | 64 | 0.20 | 0.32 |
| TAF | 10 | 0.5 | 56 | 82 | 0.50 | 0.73 |
|  |  | 2 | 34 | 140 | 0.40 | 1.69 |
|  |  | 6 | 30 | 107 | 0.54 | 1.92 |
| (2 mice) | 27 | 24 | 5 | 51 | 0.53 | 5.57 |

TABLE II

Distribution of $^{125}I$ activity in tissues of normal mice treated with liposome-entrapped second antibody and in normal control mice

|  | Counts per minute/g | | | |
|---|---|---|---|---|
|  | Liver | Kidney | Spleen | Blood |
| Liposome-treated* (3 mice) | 630498 ± 74379 | 221133 ± 10447 | 755271 ± 170083 | 613559 ± 24866 |
| Control (3 mice) | 325362 ± 43694 | 275105 ± 24859 | 237078 ± 3379 | 1071762 ± 103313 |

*Liposome dose 5 μmole lipid, 630 μg IgG. Tissues were excised 4 h after administration of liposomes.

TABLE III

Distribution of $^{99m}Tc$ activity in tissues of normal mice excised 30 min to 24 h after administration of liposome-entrapped second antibody (10 μmole lipid, 1260 μg IgG)

|  | % total $^{99m}Tc$ in whole tissue | | | | |
|---|---|---|---|---|---|
| Time (h) | 0.5 | 2.0 | 5.0 | 18.0 | 24.0 |
| Blood | 17.6 ± 0.8 | 5.4 ± 0.6 | 2.2 ± 0.4 | 0.8 ± 0.1 | 0.6 ± 0.1 |
| Liver | 42.3 ± 2.6 | 49.1 ± 2.1 | 42.9 ± 0.8 | 36.1 ± 1.5 | 19.8 ± 1.7 |
| Spleen | 2.9 ± 0.3 | 3.6 ± 1.7 | 3.4 ± 0.2 | 4.1 ± 0.4 | 2.0 ± 0.1 |
| Kidneys | 5.0 ± 0.8 | 4.2 ± 0.4 | 3.0 ± 0.2 | 1.6 ± 0.2 | 1.0 ± 0.1 |

Counts were adjusted to account for radioactive decay

TABLE IV

Distribution of $^{14}C$-cholesterol activity in xenograft-bearing mice (two animals) treated with liposome-entrapped second antibody (27 μmole lipid, 3.4 mg IgG). Tissues were excised 24 h after injection of liposomes.

| Tissue | % total counts injected remaining 24 h after liposome injection |
|---|---|
| Blood | 6.4 ± 0.1 |
| Liver | 9.1 ± 0.4 |
| Spleen | 0.8 ± 0.3 |
| Tumour | 0.003 ± 0.03 |

TABLE V

Liposomal clearance of radiolabelled IgG in rabbits

|  | % (count pre-liposome injection) rabbit number | | | | | | |
|---|---|---|---|---|---|---|---|
| Time (h) after injection of $^{125}I$-goat IgG | liposome-entrapped second antibody 1 | 2 | 3 | empty liposomes 4 | 5 | no liposomes 6 | 7 |
| (Pre-liposomes) 24 | 100.0 | 100.0 | 100.0 | 100.0 | 100.0 | 100.0 | 100.0 |
| (Post-liposomes) 24 | 100.8 | 109.9 | 88.9 | 97.4 | 103.8 | 102.5 | 103.7 |
| 26 | 62.7 | 57.9 | 72.6 | 83.0 | 90.3 | 96.3 | 80.6 |
| 48 | 50.9 | 47.5 | 57.6 | 62.6 | 55.9 | 64.3 | 65.9 |
| 72 | 33.9 | 28.8 | — | 36.3 | 39.3 | 51.4 | 56.6 |
| 120 | — | — | 7.9 | — | — | — | — |
| 144 | 7.2 | 4.9 | — | — | — | — | — |
| 168 | — | — | 4.0 | — | — | — | — |
| 192 | 2.6 | 2.0 | — | 7.5 | 7.0 | 9.9 | 13.0 |
| 216 | — | — | 2.1 | — | — | — | — |
| 240 | 0.9 | 0.8 | — | 4.5 | 3.9 | 6.6 | 7.5 |
| 288 | — | — | 0.7 | — | — | — | — |
| 312 | 0.6 | 0.7 | — | — | — | — | — |
| 360 | — | — | — | 1.4 | 0.9 | 1.7 | 2.6 |

$^{125}I$ counts were adjusted to account for radioactive decay.

EXAMPLE 2

Goat anti-CEA was prepared as described in Example 1, except that labelling was performed using $^{131}I$ instead of $^{125}I$. Liposome-linked horse anti-goat antibody was then prepared as described in Example 1. Five human patients were given between 100 and 200 μg of $^{131}I$-labelled anti-CEA (0.8–2.0 mCi) intravenously, followed 24 hours later by between 8 and 32 mg of liposome-linked antibody incorporated into 80–300 μmoles of lipid as liposomes.

As can be seen from FIG. 3, the clearance of $^{131}I$-labelled anti-CEA from human blood is accelerated in a dose-related fashion by the liposome-linked antibody of the present invention. Very significantly, $^{131}I$-labelled anti-CEA is retained in an area of tumour in the abdomen (FIG. 4). This same figure also illustrates that rapid clearance from the lungs and heart is achieved. $^{131}I$-labelled anti-CEA accumulates initially in the liver, but is then cleared rapidly, so that 48 hours after administration of liposome-linked antibody, the level of $^{131}I$ in liver is comparable to that in heart and lung.

The usefulness of the liposome-linked antibody of the present invention in detecting tumours is illustrated by FIGS. 5 and 6, which are images obtained by scanning the pelvis of a human patient after administration of $^{131}I$-labelled anti-CEA. In FIG. 5 the bladder (BL) is the predominant feature, because of non-specific accumulation of $^{131}$I. 24 hours after administration of liposome-linked antibody, however, a large proportion of the non-specifically accumulated $^{131}$I has been cleared, leaving a tumour (T) clearly visible behind the bladder (FIG. 6).

I claim:

1. A liposome to which is linked an antibody capable of binding an anti-tumor antibody, which liposome-linked antibody is, when administered to a patient, capable of clearing from extracellular spaces of said patient that portion of said anti-tumor antibody not bound to tumor.

2. A liposome having entrapped therein an antibody capable of binding an anti-tumor antibody, which liposome-entrapped antibody is, when administered to a patient, capable of clearing from extracellular spaces of said patient that portion of said anti-tumor antibody not bound to tumor.

3. A liposome according to claim 2 wherein the anti-tumor antibody is anti-carcinoembryonic antigen.

4. A method of treatment of a tumor comprising administering to a patient bearing tumor a pharmaceutically effective amount of an anti-tumor antibody and subsequently administering to said patient an effective amount of a liposome-linked antibody capable of binding said anti-tumor antibody, which liposome-linked antibody is capable of clearing from extracellular spaces of said patient that portion of said anti-tumor antibody not bound to tumor.

5. A method according to claim 4 wherein said antibody linked to said liposome is entrapped in said liposome.

6. A method according to claim 4 wherein said anti-tumour antibody is anti-carcinoembryonic antigen.

7. A method according to claim 4 wherein said anti-tumour antibody is coupled to an anti-cancer agent.

8. A method of detecting a tumor comprising administering to a patient suspected of having said tumor a diagnostically effective amount of a labelled anti-tumor antibody, and subsequently administering to said patient an effective amount of liposome-linked antibody capable of binding said anti-tumor antibody, which liposome-linked antibody is capable of clearing from extracellular spaces of said patient that portion of said anti-tumor antibody not bound to tumor.

9. A method according to claim 8 wherein said antibody linked to said liposome is entrapped in said liposome.

10. A method according to claim 8 wherein said anti-tumour antibody is anti-carcinoembryonic antigen.

11. A method according to claim 8 wherein said labelled antibody is radio-labelled.

12. A method according to claim 11 wherein said labelled antibody is $^{131}$I-labelled.

13. A method according to claim 12 wherein said $^{131}$I-labelled antibody is detected by external scintigraphy between 2 and 48 hours after administration of said second antibody.

14. A method according to claim 13 wherein said $^{131}$I labelled antibody is detected by external scintigraphy about 24 hours after administration of said second antibody.

* * * * *